United States Patent [19]
Penfold et al.

[11] Patent Number: 6,133,048
[45] Date of Patent: Oct. 17, 2000

[54] ASSAY REAGENTS AND DEVICES

[75] Inventors: Yvonne E. Penfold, Bedford; David A. Percival, Harwarden, both of United Kingdom

[73] Assignee: Unilever Patent Holdings BV, Vlaardingen, Netherlands

[21] Appl. No.: 08/935,537

[22] Filed: Sep. 23, 1997

[30] Foreign Application Priority Data

Sep. 27, 1996 [EP] European Pat. Off. .............. 96307078

[51] Int. Cl.[7] ...................... G01N 33/546; G01N 33/545; G01N 33/549; G01N 33/53
[52] U.S. Cl. .......................... 436/533; 436/531; 436/534; 436/514; 436/810; 435/970; 435/805; 422/56
[58] Field of Search ..................... 436/531, 533, 436/534, 514, 810; 435/970, 805; 422/56

[56] References Cited

U.S. PATENT DOCUMENTS

| | | | |
|---|---|---|---|
| 4,118,192 | 10/1978 | Sawai et al. ................................ | 424/12 |
| 4,224,304 | 9/1980 | Sawai et al. ................................ | 424/12 |
| 4,680,274 | 7/1987 | Sakai et al. ............................... | 436/512 |
| 4,812,414 | 3/1989 | Warren, III et al. ..................... | 436/533 |
| 5,356,782 | 10/1994 | Moorman et al. ........................ | 435/7.9 |
| 5,679,581 | 10/1997 | Miyazaki et al. ........................ | 436/517 |

OTHER PUBLICATIONS

Ed Harlow and David Lane. Antibodies: A Laboratory Manual. 1988. pp. 608 and 632.

*Primary Examiner*—Nita Minnifield
*Assistant Examiner*—Padma Baskar
*Attorney, Agent, or Firm*—Pillsbury Madison & Sutro LLP

[57] ABSTRACT

A reagent useful in immunoassays, comprising a direct particulate level co-sensitized with a specific binding agent having specificity for an analyte or analyte analog and with a non-specific protein which can participate in a control reaction with another specific binding agent which does not bind to the first specific binding agent nor participate in the formation of a complex by means of which detection of the analyte or analyte analog is accomplished. Preferably the first specific binding agent is an antibody raised in a first species and the non-specific protein is an immunoglobulin from another species. Optionally, the reagent additionally comprises a second population of the direct particulate label sensitized solely with the non-specific protein.

7 Claims, No Drawings

ASSAY REAGENTS AND DEVICES

FIELD OF THE INVENTION

This invention relates to reagents useful in immunoassays and to assay devices using such reagents.

BACKGROUND TO THE INVENTION

Many assays are now available which utilise the technology described in EP-A-291194 (equivalent to U.S. Pat. No. 5,622,871), wherein a particulate direct label such as a gold sol or coloured latex particle is used to reveal the result of an assay conducted in a porous carrier such as a porous strip. Concentration of the particulate label in a comparatively small detection zone in the strip reveals the assay result. It is common practice for the strip to include a control zone, normally located downstream from the detection zone, in which a coloured signal is also generated to reassure the user that the test has been correctly performed. In most commercial products based on this concept, the test and control signals are generated using the same particulate label.

This technology copes very well with most assay situations, but there can be extreme situations in which the clarity of the signals could be improved. For example, the control zone signal may appear rather faint if the concentration of analyte is very high and is causing most of the particle label to become bound in the detection zone, leaving insufficient label to carry through and provide a strong control signal.

An objective of the present invention is to provide reagents and assay devices in which improved clarity of assay signals are obtained irrespective of the amount of analyte that may be present in a sample being tested.

A further objective is to provide good clear assay signals without the use of excessive amounts of labelled reagent.

GENERAL DESCRIPTION OF THE INVENTION

By the invention we provide a reagent useful in immunoassays, comprising a direct particulate label co-sensitised with a specific binding agent having specificity for an analyte or analyte analogue and with a non-specific protein which can participate in a control reaction with another specific binding agent which does not bind to the first specific binding agent nor participate in the formation of a complex by means of which detection of the analyte or analyte analogue is accomplished.

Preferably the quantity of specific binding agent on the co-sensitised particle exceeds the quantity of non-specific protein thereon. Preferably there is at least a 2:1 ratio by weight between these two materials on the particle. More preferably at least about 5:1, ideally about 10:1. The primary specific activity, in terms of analyte-binding and control signal formation, is therefore heavily biassed in favour of analyte-binding.

Optionally, the reagent additionally comprises a second population of the direct particulate label sensitised solely with the non-specific protein.

Preferably the first specific binding agent is an antibody raised in a first species and the non-specific protein is an immunoglobulin from another species. For example, the first specific binding agent can be a murine antibody.

The non-specific protein can be a rabbit immunoglobulin, for example, but any immunoglobulin from any species can be used provided that it does not bind either to the analyte or to any reagent that participates in detection of the analyte.

A preferred reagent according to the invention comprises coloured latex particles of diameter less than 0.5 micron, co-sensitised with an anti-hCG murine monoclonal antibody and with rabbit IgG. Preferably this reagent additionally comprises same-coloured latex particles of diameter less than 0.5 micron sensitised solely with rabbit IgG, the weight ratio of the co-sensitised particles to the second particles being at least 2:1, more preferably about 3:1.

Another embodiment of the invention is an assay device of the type wherein a sample liquid reconstitutes a labelled reagent and carries it into a detection zone and a control zone, binding of the labelled reagent in these zones revealing the assay result, characterised in that the labelled reagent is as described in any one of the foregoing paragraphs.

Preferably the detection zone contains an immobilised specific binding agent which acts as a direct or indirect capture means for the analyte or analyte analogue but which does not bind to the non-specific protein, and the control zone contains a specific binding agent which binds the non-specific protein but does not bind the specific binding agent co-sensitised on the first particle.

The particles can be any micro-particles that can be used as mobile labels in strip-format assays. Such assays are described in many publications, including EP-A-291194, EP-A-383619, WO 96/09553 and WO 96/09546. Appropriate particles include latex (polystyrene) particles, usually of diameter less than about 0.5 micron, metal sols, such as gold sols, non-metallic elemental sols, such as selenium or carbon, and dye sols.

The invention will be described with particular reference to test kits useful in monitoring of body fluid analytes, and especially to home monitoring of urinary analytes of relevance to the determination of pregnancy (hCG) or of the fertility status of the human ovulation cycle (by measuring LH and/or E3G and/or P3G, for example). This is by way of example only, and it will be appreciated that the invention is useful in many other contexts where other sample liquids and analytes are involved, such as assays for cancer markers, cardiac markers, blood glucose, drugs of abuse, hormones, infectious disease markers, tests in therapeutic drug monitoring, manufacturing and raw material quality control, and tests for effluent and pollution levels.

Preferably the detection zone contains an immobilised is specific binding agent which acts as a direct or indirect capture means for hCG, the control zone contains an immobilised anti-rabbit IgG antibody, and the mobile labelled reagent comprises coloured latex particles of diameter less than 0.5 micron, co-sensitised with an anti-hCG murine monoclonal antibody and with rabbit IgG.

Preparation of the novel reagents of the invention, and the manufacture of assay devices using these novel reagents, can both be accomplished using conventional procedures. The co-sensitised particulate label can be prepared by contacting commercially-available particulate labels, such as latex (polystyrene) particles of appropriate dimension, in aqueous suspension with a mixture of the two materials with which the particles must be sensitised. For example, these materials can be a mixture of a murine monoclonal antibody directed against the alpha-chain of hCG, together with a non-specific polyclonal antibody such as rabbit IgG. These materials need to be present in an appropriate weight ratio, as described elsewhere herein. The co-sensitisation needs to be conducted under buffered conditions, as is standard practice. Following a sufficient time interval to allow the materials to deposit onto the particles, unbound materials can be separated by conventional procedures such as centrifugation, filtration and/or ultra-filtration and the co-sensitised particles resuspended in a conventional storage buffer solution ready for use in the preparation of an assay. A specific example of a co-sensitisation procedure is given below.

In order to describe the benefits of the invention in more detail, we can consider as an example its applicability in the context of a pregnancy test based on the immunochromatographic format using coloured latex particles as a mobile direct label in an assay strip. The assay strip, which is, for example, made from nitrocellulose of pore size about 8 microns backed with "Mylar" polyester, includes two transverse lines of deposited immobilised specific binding reagents, namely a test line containing an anti-β hCG murine monoclonal and a control line downstream from the test line containing an immobilised murine monoclonal raised against rabbit IgG. At a location upstream from the test line is a mobile reagent comprising coloured latex particles of diameter approximately 0.3 microns. This location can be on the nitrocellulose or in a separate pad or wick of porous material which is upstream in the flow path by which sample liquid (urine) can reach the nitrocellulose. The mobile reagent comprises two populations of latex particles, namely:

a) particles co-sensitised with an anti-α hCG murine monoclonal and with the same rabbit IgG against which the control line antibody was raised; and b) a second population of the same latex particles simply bearing the rabbit IgG.

Application of a urine sample will mobilise the latex particles. If the urine contains hCG, a sandwich complex can form between the anti-hCG monoclonal on the co-sensitised particle and the anti-hCG antibody in the test line. In consequence, at least some of the co-sensitised particles will become bound in the test line to provide a coloured signal indicative of the presence of hCG. Remaining mobilised co-sensitised particles which do not become bound in the test line, eg. because they are in excess relative to the amount of hCG present in the sample, can become bound downstream in the control line by interaction between the control line antibody and the rabbit IgG on the co-sensitised particles. In addition, the second population of latex particles bearing only the rabbit IgG will be mobilised and carried past the test line to reinforce the control signal.

We have found in practice that if the hCG concentration in the urine sample is comparatively high (although not so high as to induce the well-known "hook effect" which causes a drop in the apparent hCG signal) most of the anti-hCG particles are bound in the test line. Typically this will occur if the hCG concentration lies between about 5000 and about 15000 mIU/ml. Under these circumstances there would be a strong test line signal but a rather faint or completely absent control line signal. However, the provision of the second population of latex particles, which cannot possibly bind in the test line, ensures that a strong control line signal is still obtained even under these circumstances. An appropriate blend of the co-sensitised particles and the mono-sensitised particles is about 3:1. In a sandwich-format assay this combination of particles provides a good clear test signal and control signal under most assay conditions, with the exception of extremely high analyte concentrations, while requiring the minimum total number of particles. Substantially more particles would be required if the test signal and control signal were generated by completely separate populations.

EXAMPLE

This example describes a sensitisation procedure which can be used to prepare reagents in accordance with the invention.

A latex particle reagent co-sensitised with a murine anti-α hCG monoclonal antibody and with rabbit immunoglobulin can be prepared as follows.

10 ml of a commercially available suspension (10% solids) of blue coloured latex particles of diameter about 0.3 microns is added to 40 ml of 100 mM borate buffer pH 8.5 and stirred vigorously. This mixture is centrifuged for 10 minutes at 13500 rpm and the supernatant liquid removed. The latex pellet is re-suspended in 20 ml of the same buffer.

To a separate 20 ml of the same buffer are added 400 μg/ml of a murine anti-β hCG monoclonal antibody and 50 μg/ml rabbit IgG. The latex-containing buffer and the antibody-containing buffer are both heated in a water bath to 40° C. and, on reaching this temperature, 5 ml of ethanol is added to each. The antibody solution is then immediately added to the latex suspension, mixed using a magnetic stirrer, and incubated in the water bath for 60 minutes. At this point 50 ml of a solution of bovine serum albumin (BSA) in the same buffer pre-warmed to 40° C. is added and the incubation continued at 40° C. for a further 30 minutes. Thereafter the solution is centrifuged for 25 minutes at 13500 rpm and the supernatant removed. The pellet is resuspended in 50 ml of 100 mM Tris buffer pH 9.0 to provide a suspension containing 2% solids. Optionally preservatives such as sucrose at 20% (w/v) and BSA at 10% (w/v) can be added. This latex suspension is ready for use in the preparation of an assay device.

An identical procedure can be used to prepare latex particles sensitised solely with the rabbit immunoglobulin. In this instance the 20 ml suspension of latex particles is combined with 20 ml buffer containing 150 μg/ml rabbit IgG.

In the subsequent preparation of an assay device using a combination of the co-sensitised and mono-sensitised particles, the two suspensions of sensitised particles can be combined in appropriate proportions (to provide an appropriate blend, e.g. 3 to 1 of the two populations of particles) and applied as a single combined reagent on a test strip or in a separate pad or wick forming part of an assay device.

What is claimed is:

1. A reagent useful in immunoassays, comprising a direct particulate label co-sensitized with (i) a specific binding agent having specificity for an analyte or analyte analogue, and (ii) a non-specific protein which does not bind to said analyte or analyte analogue but can participate in a control reaction with another specific binding agent which does not bind to said first specific binding agent nor participate in the formation of a complex by means of which detection of said analyte or analyte analogue is accomplished, said specific binding agent being a murine antibody and said non-specific protein being a rabbit immunoglobulin.

2. A reagent according to claim 1, further comprising a population of direct particulate label sensitized solely with said non-specific protein.

3. A reagent according to claim 1, comprising coloured latex particles of diameter less than 0.5 micron, co-sensitised with an anti-hCG murine monoclonal antibody and with rabbit IgG.

4. A reagent according to claim 3, additionally comprising same-coloured latex particles of diameter less than 0.5 micron sensitised solely with rabbit IgG, the ratio of said co-sensitised particles to said additional latex particles being at least 2:1.

5. A reagent according to claim 4, wherein said ratio is about 3:1.

6. A reagent according to claim 1 wherein the quantity of specific binding agent on the co-sensitized particulate exceeds the quantity of non-specific protein therein.

7. A reagent according to claim 6 wherein the ratio of specific binding agent to non-specific protein is at least 5.1.

* * * * *